United States Patent
Srinivasan et al.

(10) Patent No.: US 11,577,030 B2
(45) Date of Patent: Feb. 14, 2023

(54) PEN NEEDLE ATTACHMENT MECHANISMS

(71) Applicant: Embecta Corp., Andover, MA (US)

(72) Inventors: Sudarsan Srinivasan, Hawthorne, NJ (US); MichaeL DiBiasi, Pompton Plains, NJ (US); Sean Sullivan, Ridgewood, NJ (US); Keith Knapp, II, Warwick, NY (US); Joshua Herr, Cary, NC (US); Amit Limaye, Wayne, NJ (US); David Huang, Hayward, CA (US); David Schiff, Highland Park, NJ (US); Todd Sack, Dover, DE (US)

(73) Assignee: Embecta Corp., Andover, MA (US)

( * ) Notice: Subject to any disclaimer, the term of this patent is extended or adjusted under 35 U.S.C. 154(b) by 320 days.

(21) Appl. No.: 15/637,239

(22) Filed: Jun. 29, 2017

(65) Prior Publication Data
US 2017/0361027 A1 Dec. 21, 2017
US 2018/0369496 A9 Dec. 27, 2018

Related U.S. Application Data

(63) Continuation of application No. 15/100,275, filed as application No. PCT/US2014/068498 on Dec. 4, 2014, now Pat. No. 10,709,846.
(Continued)

(51) Int. Cl.
*A61M 5/00* (2006.01)
*A61M 5/32* (2006.01)
*A61M 5/34* (2006.01)

(52) U.S. Cl.
CPC .......... *A61M 5/3202* (2013.01); *A61M 5/002* (2013.01); *A61M 5/347* (2013.01); *A61M 2205/581* (2013.01); *A61M 2205/582* (2013.01)

(58) Field of Classification Search
CPC .. A61M 5/343; A61M 5/3202; A61M 5/3213; A61M 5/3293; A61M 5/347;
(Continued)

(56) References Cited

U.S. PATENT DOCUMENTS 4,040,421 A 8/1977 Young
4,125,588 A 11/1978 Hansen et al.
(Continued)

FOREIGN PATENT DOCUMENTS

CN 102395396 A 3/2012
JP S53-142088 A 12/1978
(Continued)

OTHER PUBLICATIONS

International Preliminary Report on Patentability and Written Opinion dated Aug. 1, 2017 which issued in the corresponding Application No. PCT/US2016/015680.
(Continued)

*Primary Examiner* — Bhisma Mehta
*Assistant Examiner* — William R Frehe
(74) *Attorney, Agent, or Firm* — Greenberg Traurig, LLP; David J. Dykeman; Roman Fayerberg

(57) ABSTRACT

User-friendly attachment mechanisms for pen needles provide improved handling and ease of use, including locking installation and removal features and sensory feedback when a needle-bearing hub is seated on a pen.

16 Claims, 19 Drawing Sheets

Related U.S. Application Data

(60) Provisional application No. 61/931,085, filed on Jan. 24, 2014, provisional application No. 61/911,716, filed on Dec. 4, 2013.

(58) Field of Classification Search
CPC ...... A61M 2205/581; A61M 2205/582; A61M 5/32; A61M 5/3216; A61M 2005/3217; A61M 5/3219; A61M 2005/3104; A61M 2005/3118; A61M 2005/312
See application file for complete search history.

(56) References Cited

U.S. PATENT DOCUMENTS

| | | | |
|---|---|---|---|
| 5,352,200 A * | 10/1994 | Hammett | A61M 5/3216 604/110 |
| 5,738,232 A | 4/1998 | Roberts et al. | |
| 6,843,781 B2 | 1/2005 | Alchas et al. | |
| 7,645,264 B2 | 1/2010 | Marsh et al. | |
| 8,057,444 B2 | 11/2011 | Hartmann et al. | |
| 10,709,846 B2 | 7/2020 | Srinivasan et al. | |
| 2004/0236284 A1 * | 11/2004 | Hoste | A61M 5/326 604/198 |
| 2007/0293819 A1 | 12/2007 | Giambattista et al. | |
| 2007/0299394 A1 * | 12/2007 | Rolfe | A61M 5/3205 604/110 |
| 2008/0281264 A1 * | 11/2008 | Reid | A61M 5/31 604/110 |
| 2009/0069753 A1 * | 3/2009 | Ruan | A61M 5/3202 604/192 |
| 2009/0069755 A1 * | 3/2009 | Horvath | A61M 5/46 604/240 |
| 2011/0040280 A1 | 2/2011 | Ijitsu et al. | |
| 2011/0077602 A1 * | 3/2011 | Yokota | A61M 5/32 604/239 |
| 2011/0118667 A1 | 5/2011 | Zaiken et al. | |
| 2012/0022460 A1 | 1/2012 | Horvath et al. | |
| 2012/0041381 A1 | 2/2012 | Raj et al. | |
| 2012/0071835 A1 * | 3/2012 | Marshall | A61M 5/3202 604/192 |
| 2012/0109052 A1 * | 5/2012 | Wei | A61M 5/3202 604/82 |
| 2012/0191046 A1 * | 7/2012 | Larsen | A61M 5/3202 604/192 |
| 2014/0343507 A1 | 11/2014 | Karlsson et al. | |
| 2015/0065961 A1 * | 3/2015 | Daniel | A61M 5/3213 604/198 |
| 2015/0297837 A1 | 10/2015 | Schraga | |
| 2017/0021110 A1 | 1/2017 | Srinivasan et al. | |
| 2017/0128676 A1 * | 5/2017 | Spallek | A61M 5/2466 |
| 2017/0197039 A1 | 7/2017 | Shiozaki et al. | |
| 2018/0110932 A1 * | 4/2018 | Trosborg | A61M 5/347 |
| 2020/0297938 A1 | 9/2020 | Srinivasan et al. | |

FOREIGN PATENT DOCUMENTS

| | | |
|---|---|---|
| JP | H08-299440 A | 11/1996 |
| JP | 2004-504891 A | 2/2004 |
| JP | 2004-305749 A | 11/2004 |
| JP | 2004305749 | 11/2004 |
| JP | 2006-517129 A | 7/2006 |
| JP | 2009-90098 A | 4/2009 |
| JP | 2009-090098 A | 4/2009 |
| JP | 2009-101140 A | 5/2009 |
| JP | 2009101140 A | 5/2009 |
| JP | 2012-519546 A | 8/2012 |
| JP | 2012-519546 A | 8/2012 |
| JP | 2012519546 | 8/2012 |
| JP | 2012-523876 A | 10/2012 |
| JP | 2012-529322 A | 11/2012 |
| JP | 2013-138879 A | 7/2013 |
| JP | 2013138879 | 7/2013 |
| JP | 5385260 B2 | 10/2013 |
| JP | 5385260 B2 | 1/2014 |
| WO | WO-02100467 A2 | 12/2002 |
| WO | WO-2012085579 A2 | 6/2012 |
| WO | WO-2014105905 A2 | 7/2014 |
| WO | WO-2014154605 A1 | 10/2014 |
| WO | 2015-186792 A1 | 12/2015 |

OTHER PUBLICATIONS

European Communication Pursuant to Article 94(3) EPC dated Jul. 19, 2019, which issued in the corresponding European Patent Application No. 14 867 037.5.

Chinese Office Action dated Apr. 2, 2021, which issued in the corresponding Chinese Patent Application No. 201680001274.X, including Eng. translation.

Japanese Office Action dated Sep. 29, 2020, which issued in the corresponding Japanese Patent Application No. 2019-194437, including Eng. translation.

Japanese Office Action dated Jun. 22, 2021, which issued in the corresponding Japanese Patent Application No. 2020-158848, including Eng. translation.

* cited by examiner

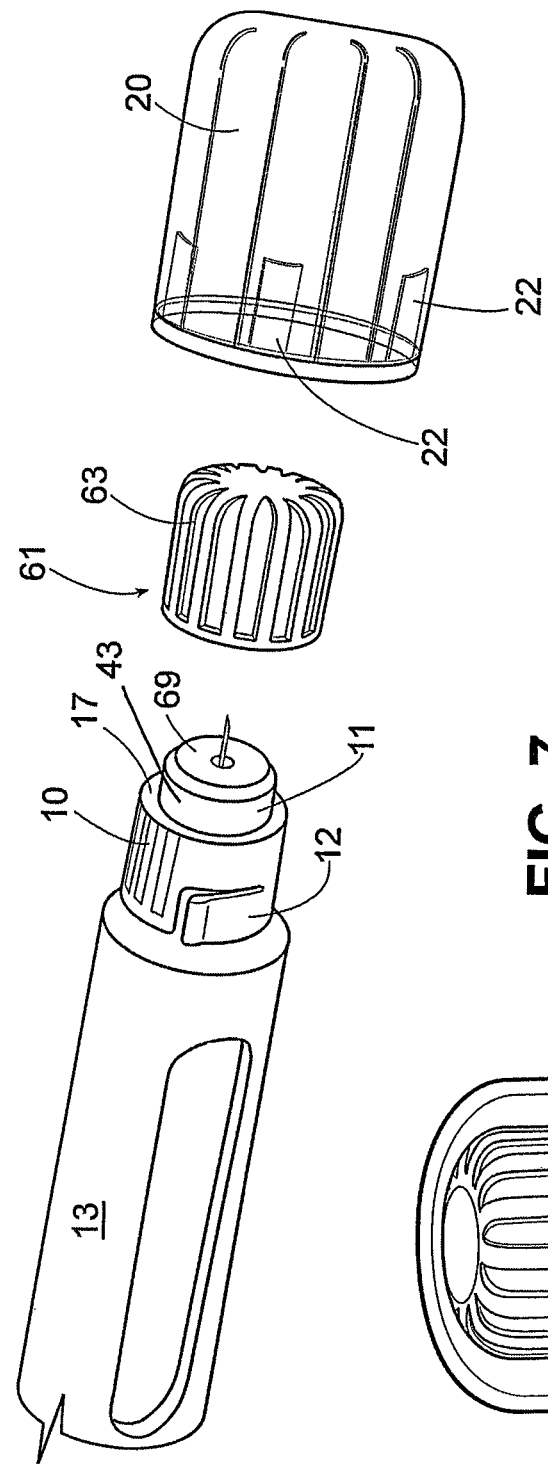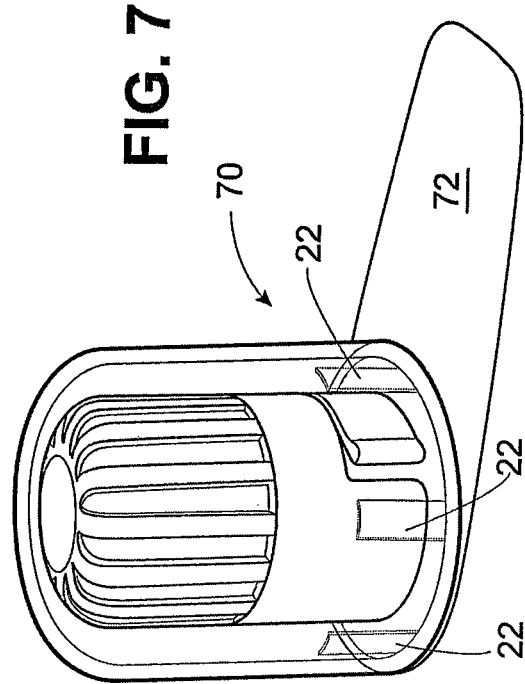

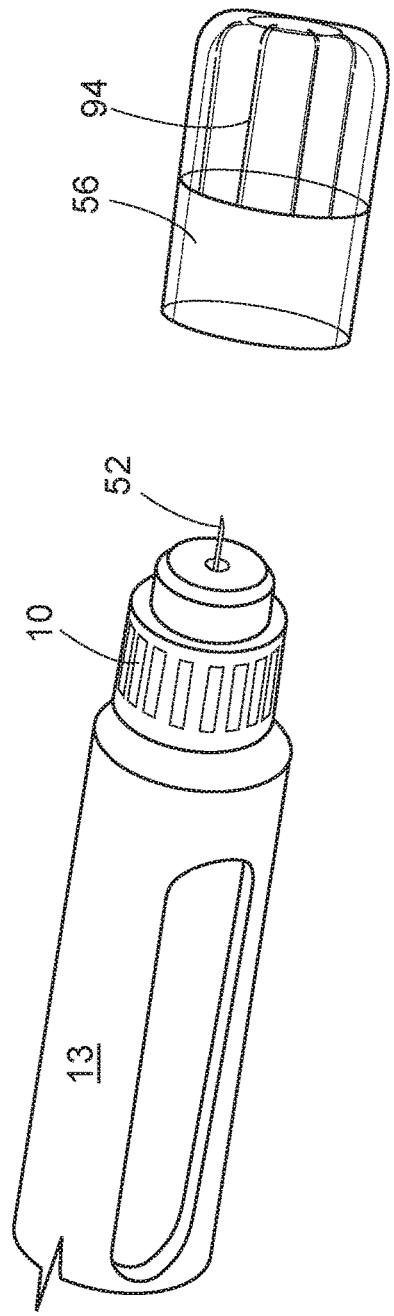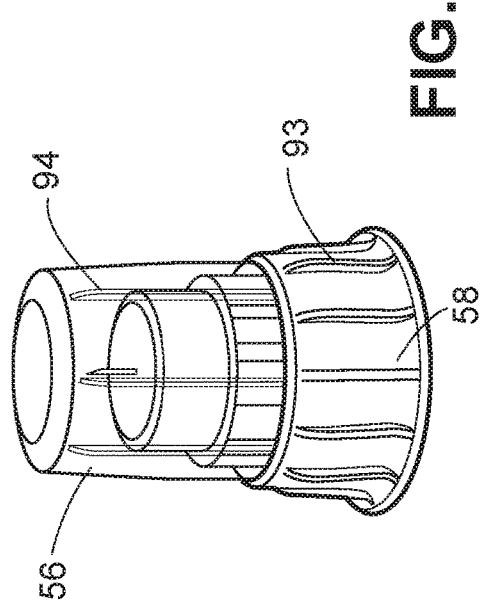

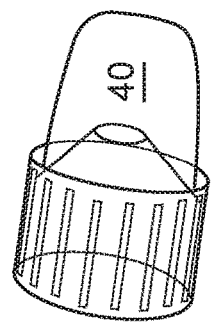
FIG. 13
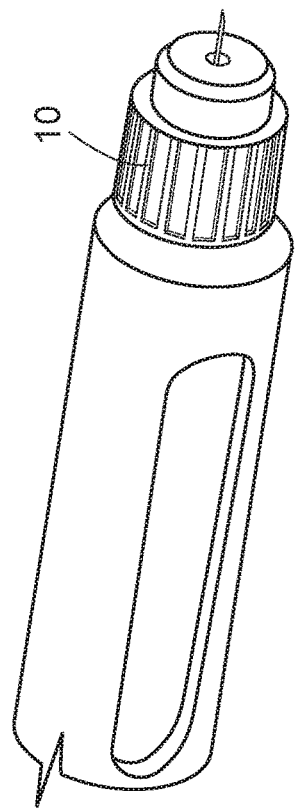
FIG. 14
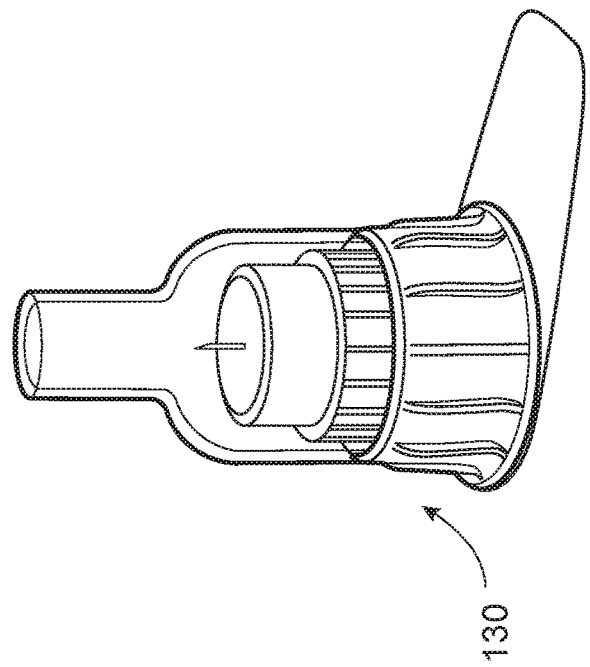

PEN NEEDLE ATTACHMENT MECHANISMS

CROSS REFERENCE TO RELATED APPLICATIONS

This application is a continuation of U.S. application Ser. No. 15/100,275 filed May 17, 2016, which is a § 371 application of PCT/US2014/068498, which claims the benefit of U.S. Provisional Application No. 61/911,716, filed on Dec. 4, 2013, and U.S. Provisional Application No. 61/931,085, filed on Jan. 24, 2014, which are incorporated in their entirety herein by reference.

BACKGROUND OF THE INVENTION

Field of the Invention

The invention is directed to pen needles adapted for attachment to a medication delivery device such as a medication pen. The pen needles according to the invention have attachment mechanisms that provide sensory feedback, such as an audible clicking sound or tactile sensation when the needle-bearing hub is fully seated on the medication pen, and other features that enhance ease of use.

Description of the Related Art

Pen needles are used to attach to a medication pen and are especially popular for delivering self-administered injectable medications such as insulin. In one well known commercial device, a needle-bearing hub is provided inside a funnel-shaped outer cover, sometimes referred to as the "outer shield," or simply as the "cover." The cannula is affixed in an axial bore of the hub with one end protruding from the distal or "patient side" of the hub, and the other end of the needle is recessed in a cavity on the proximal or "non-patient" side of the hub, adapted for attachment to the medication pen. A paper and foil "teardrop" label is heat sealed on the edge of the open end of the funnel shaped outer cover. In addition, the medication pen may have a cap received over the distal end of the medication pen, over the opening where the pen needle is installed. To install the pen needle on a medication pen, the user removes the medication pen cap. The user then removes the label on the pen needle outer cover and holds the outer cover to install the hub, typically threading the hub onto the pen. Once the hub is installed on the medication pen, the outer cover can be removed by pulling the outer cover distally off the hub. A separate inner needle shield sits over the needle, which the user must remove to administer an injection. The inner shield generally sits on the hub and simply helps the user locate the needle without forming a sterility barrier. After use, the user may use the outer cover to unthread the hub from the pen and dispose of the pen needle.

Medication pens and associated pen needles are disclosed in U.S. Pat. No. 7,645,264, and U.S. Patent Application Publication Nos. 2009/0069755 and 2012/0022460, all of which are incorporated by reference in their entirety for their teaching of pen needle design and construction. A device for releasably arranging a pen needle on an injection pen and releasing the pen needle into a mating storage or disposal container is disclosed in U.S. Pat. No. 8,057,444, also incorporated by reference.

With the prior art described above, it is not always possible for the user to tell that the hub is properly seated on the medication pen. The pen does not provide a sensory feedback that the pen needle is seated on the pen (other than the tightening of the threaded connection itself). This can lead to over-tightening the pen needle on the pen, which would render the pen needle difficult to remove, or under-tightening the pen needle on the pen, which could cause the pen needle to leak. Likewise, when removing the needle, the outer cover does not always align properly over the hub and it may take two or more tries to unscrew the hub. Although passively shielded pens are known, including pens which shield the non-patient end of the needle automatically after use, many pens simply leave the non-patient end of the needle exposed after use, relying on the proximal end cavity to provide protection from accidental needle sticks after use. It would be desirable to have a pen needle which addressed these perceived drawbacks of the prior art.

SUMMARY OF THE INVENTION

Thus one object of the invention is to provide sensory feedback when a pen needle is seated securely on a medication pen. "Sensory feedback" includes an audible or tactile sensation other than merely a feeling that the pen is tightly screwed on or loose. Another object of the invention is to use less plastic material in pen needle construction and provide features to enhance ease of use. Still another object of the invention is to provide improved sterility barriers on pen needles, to prevent contamination while allowing a medication pen cap to be placed over a pen needle installed on a medication pen.

These and other objects of the invention are achieved, in one aspect, with a pen needle comprising: a needle-bearing hub having threads or other means for attachment to a medication delivery device and at least one circumferentially oriented flexible tab located proximally of the threads. An outer cover received over the hub has at least one radially inward projection engaging the at least one flexible tab on the hub to provide sensory feedback for the user when the hub is installed onto the medication pen by rotating the outer cover.

In one embodiment, the outer cover rotates with the hub while the hub is being installed on a medication pen, but once the hub is fully seated, the outer cover rotates with respect to the hub, and no further tightening of the hub on the pen occurs. This is accompanied by audible and tactile feedback for the user. This object is achieved with a pen needle comprising: a needle-bearing hub having threads for attachment to a medication delivery device and two circumferentially oriented flexible tabs located proximally of the threads. Each flexible tab has a radially outward surface with a projection, and each projection has a beveled side. An outer cover is provided having a plurality of radially inward ribs, each rib having a beveled surface engaging the beveled surfaces of the projections on the flexible tabs, such that the flexible tabs on the hub deflect and ride over the ribs on the outer cover when the outer cover rotates with respect to the hub, creating an audible and/or tactile indication that the hub is fully installed on the medication pen without further tightening the hub on the medication pen.

In another embodiment, the outer cover rotates with the hub while the hub is being installed on a medication pen. When the hub reaches desired tightness, the device provides an audible click, or series of clicks, before the outer cover engages a hard stop on the hub. In this aspect, a pen needle according to the invention comprises: a needle-bearing hub having threads for attachment to a medication delivery device, at least one stop on the hub located proximally of the threads projecting in a radially outward direction; at least one circumferentially oriented flexible tab on the hub located proximally of the threads, each flexible tab having a radially outward projection; a circumferential gap separating the radially outward projection on the flexible tab from the stop member; an outer cover having at least one radially inward projecting rib; wherein said projection on the flexible tab rides over the rib on the outer cover when the outer cover rotates with respect to the hub to attach the pen needle to a medication pen, creating an audible and/or tactile indication that the hub is fully installed on the medication pen.

In embodiments, the flexible tab may be provided at the proximal end of the hub, proximate the opening in the hub where the medication pen is received. Alternatively, flexible tab is provided at a distal portion of the hub, for example at a step where a narrower distal end portion meets a wider proximal base portion. This arrangement permits a slimmer profile outer cover to be provided over the needle, while the base of the hub is still wide enough to accommodate a conventional threaded opening of a medication pen.

According to another embodiment of the invention, the outer cover receiving the hub snaps to a release position after the hub is fully seated on the medication pen. A pen needle according to this embodiment comprises: a needle-bearing hub having threads or other means for attachment to a medication delivery device and one circumferentially oriented flexible tab located proximally of the threads. The hub has a radially outward surface including a step portion forming a locking surface on the hub perpendicular to the axis of the needle. The outer cover received over the hub has a closed distal end, an open proximal end, and a locking rib at the open proximal end projecting radially inward and abutting the locking surface on the hub. The flexible tab has a radially outward projection positioned at one end of the step portion on the hub. The locking rib engages the projection on the flexible tab on the hub and causes the outer cover to rotate together with the hub when the hub is rotated for installation on the medication pen. When sufficient force develops between the outer cover and the hub after the hub is fully seated on the medication pen, the locking rib rides over the projection on the flexible tab on the hub deflecting the flexible tab radially inward. The locking rib is then positioned in a release channel where the locking rib is freed from the locking surface and the outer cover can be removed. The locking rib thus snaps into a position where it can be released with audible and/or tactile feedback to the user.

In another aspect of the invention a tortuous path barrier is used to obviate the conventional tear drop label. For this purpose, an outer cap and an outer cover are used, joined by a tortuous path barrier to ensure sterility. Alternatively, the foil or paper-foil label may be received on the proximal side of the hub, instead of the outer cover, and the outer cover may be received over the hub with a tortuous path barrier, dispensing with the customary inner shield received over the cannula.

A pen needle according to the invention may also incorporate features to restrict access to the needle until the hub has been fully seated on a medication pen. In embodiments, this is achieved using symmetrically placed tabs on the radially inward surface of the pen needle outer cover which engage corresponding slots on a radially outward surface of the hub. A first slot on the hub has a distal locking edge perpendicular to the axis of the needle which engages a corresponding tab on the outer cover to prevent distal movement of the outer cover with respect to the hub when the tab is engaged with the first slot. A second slot on the hub has an open distal end, so that the outer cover can move distally with respect to the hub when the tab is engaged with the second slot. The outer cover can be rotated from a first position engaging the first slot to a second position engaging the second slot after the hub is fully seated on the medication pen.

In another aspect, the invention is a pen needle having a patient end shield and a non-patient end shield which attach directly to the needle bearing hub, thus eliminating the outer cover and the paper-foil label of the currently available pen needles while retaining required functionality.

In another aspect of the invention, a pen needle hub is provided with a slim profile, having a step at a distal end thereof, so that the distal end is narrower than a proximal base portion. This permits an outer cover over the needle to be received under a conventional injection pen cap while at the same time, means for an audible and/or tactile feedback are provided to indicate to the user when the hub is installed. For this purpose, molded features on the distal portion of the hub are provided at the step portion of the hub, where the proximal base portion meets the narrower distal end portion.

BRIEF DESCRIPTION OF THE DRAWINGS

FIG. 6 is an exploded view of a medication pen and pen needle assembly incorporating the embodiment of FIG. 1.

FIG. 7 depicts the pen needle and outer cover assembly of FIG. 1 in sterile packaging.

FIG. 9 is an exploded view of a medication pen and pen needle assembly incorporating the outer cover assembly of FIG. 5.

FIG. 10 is a perspective view of the pen needle and outer cover assembly of FIG. 5 in sterile packaging.

FIG. 13 is an exploded view of medication pen and pen needle assembly incorporating the outer cover and hub assembly of FIG. 4.

FIG. 14 is a perspective view of the pen needle and outer cover assembly of FIG. 4 in sterile packaging.

The Figures are not to scale, and some features are omitted in certain views to better illustrate other features.

DETAILED DESCRIPTION OF THE PRESENT INVENTION

As used herein, the "distal" direction is in the direction of the injection site, and the "proximal direction" is the opposite direction. The "axial" direction is along the longitudinal axis of the injection device. The needle cannula is generally arranged axially in the device. "Radially" is a direction perpendicular to the axial direction. Thus, "radially inward" generally means closer to the needle. "Circumferentially" means arranged around the circumference, so that threads are arranged circumferentially on the end of a threaded fitting. The "top" view of a pen needle is looking at the pointed end of the needle.

Figure 1:
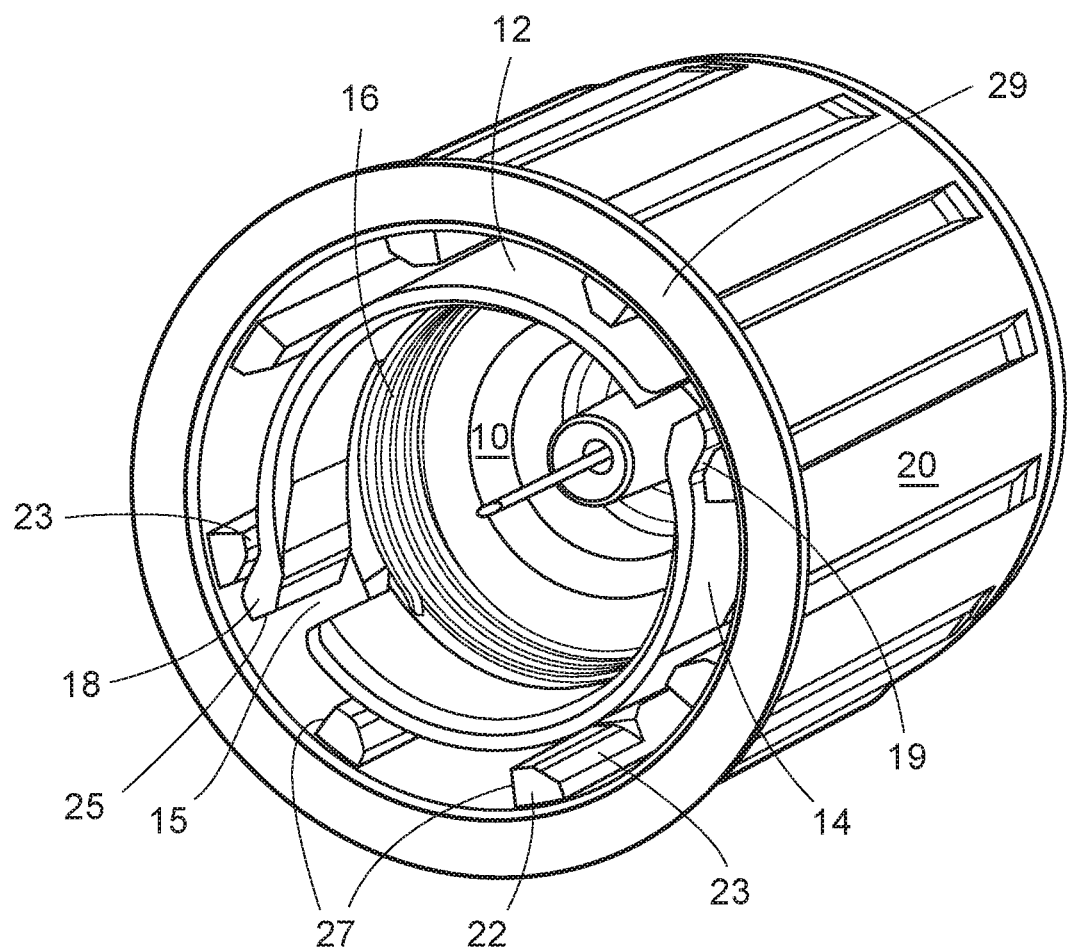
FIG. 1 is a perspective view from the non-patient side of a hub assembly with an outer cover according to one embodiment of the invention.

In the configuration shown in FIG. 1, hub 10 is provided with threads 16 arranged circumferentially in a cavity on the non-patient side of hub 10, adapted for attachment to a medication pen. At least one flexible tab 12, 14 is provided on the proximal side of the hub threads to engage an outer cover 20 as described below. In the embodiment shown, a pair of flexible tabs 12, 14 is circumferentially arranged on the proximal side of hub threads 16 and spaced apart by gap 15. In the example depicted, flexible tabs 12, 14 are at radially opposite positions on the hub, about 180 degrees apart. Flexible tabs 12, 14 engage one or more internal ribs 22 projecting from a radially inward surface of the outer cover 20 when hub 10 is threaded onto a medication pen. Outer cover 20 has an open proximal end in which the hub is received, defined by a circular edge 29. Ribs 22 on outer cover 20 engage projections 18 on the ends of the flexible tabs 12, 14 as the hub is rotated onto the medication pen. When hub 10 is initially installed on the medication pen, very little force is developed between flexible tabs 12, 14 and ribs 22 on the internal surface of outer cover 20; thus, outer cover 20 and hub 10 rotate together. Once hub 10 is fully installed, turning outer cover 20 further causes flexible tabs 12, 14 to deflect, ride over internal ribs 22, and snap into spaces between ribs 22 with an audible and/or tactile click, indicating that hub 10 is fully seated. This also ensures that hub 10 is not over-tightened because further turning force applied to outer cover 20 is not transmitted to hub 10.

Outer cover 20 and hub 10 may be configured so that engagement of hub 10 with outer cover 20 prevents the outer cover from moving distally with respect to hub 10 until after the hub is fully seated. For example, and as discussed in connection with another aspect of the invention, distal side of an internal rib 22 on outer cover 20 may abut an interference surface on a surface of the hub, so that rotating outer cover 20 with respect to the hub brings rib 22 out of engagement with the interference surface and frees outer cover 20 to move distally so that the user can remove outer cover 20 only after the audible and/or tactile feedback is obtained.

The one or more flexible tab projections 18 and the one or more internal ribs 22 on the outer cover 20 are preferably beveled on one side while the other side is straight, perpendicular to a circumferential direction (perpendicular to a line tangent to the circular opening of the outer cover). In this way, when outer cover 20 is rotated in one direction with respect to hub 10 (e.g., clockwise), the beveled side of a flexible tab projection 19 contacts the beveled side 23 of internal rib(s) 22, so that projection 18 on flexible tab 12, 14 can be deflected over rib(s) 22. Projections 18 on each flexible tab 12, 14 are at the end of the flexible tab which experiences the greatest displacement when the flexible tab is deflected. Each such projection 18 may ride over more than one rib 22 in the course of outer cover 20 being turned, making a ratchet sound. In the counterclockwise direction, when flat side 27 of rib 22 on outer cover 20 contacts flat side 25 of projection 18 on flexible tab 12, 14 on hub 10, the flexible tab does not deflect around the rib. Instead, hub 10 rotates with rotation of the outer cover 20. In this way, the user is aided removing the hub with the outer cover. This embodiment of the invention may also incorporate a retainer to prevent hub 10 from sliding out of the outer cover 20 prior to being installed on a medication pen.

Figure 21A:
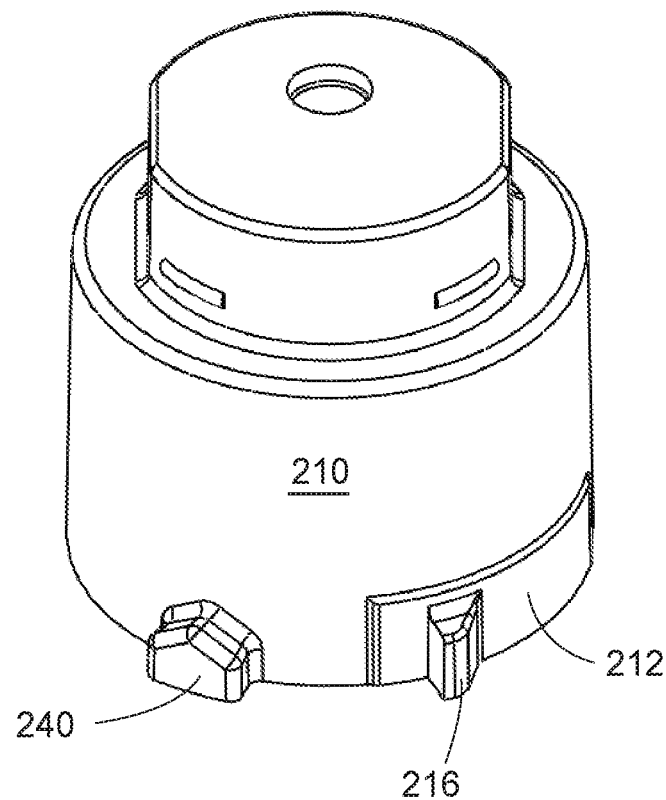
FIG. 21A depicts a hub with a sensory feedback mechanism according to an embodiment of the invention.
Figure 21B:
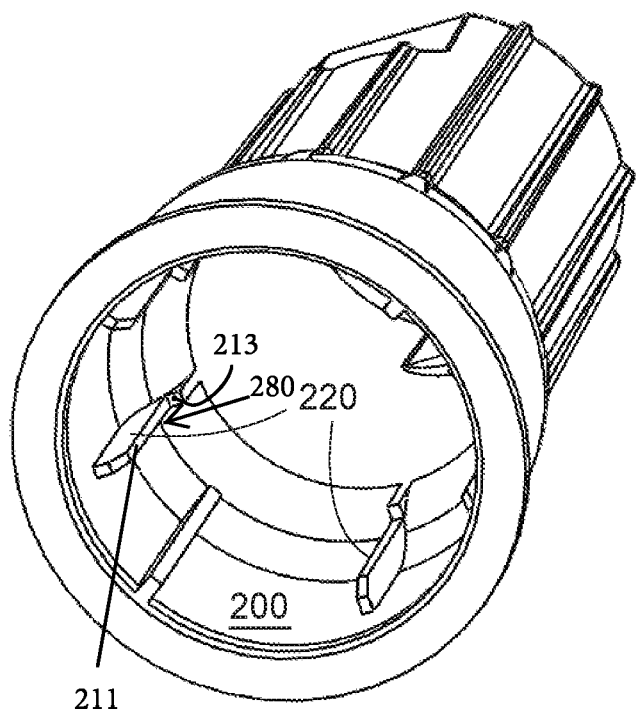
FIG. 21B depicts an outer cover adapted to engage the hub shown in FIG. 21A.
Figure 22:
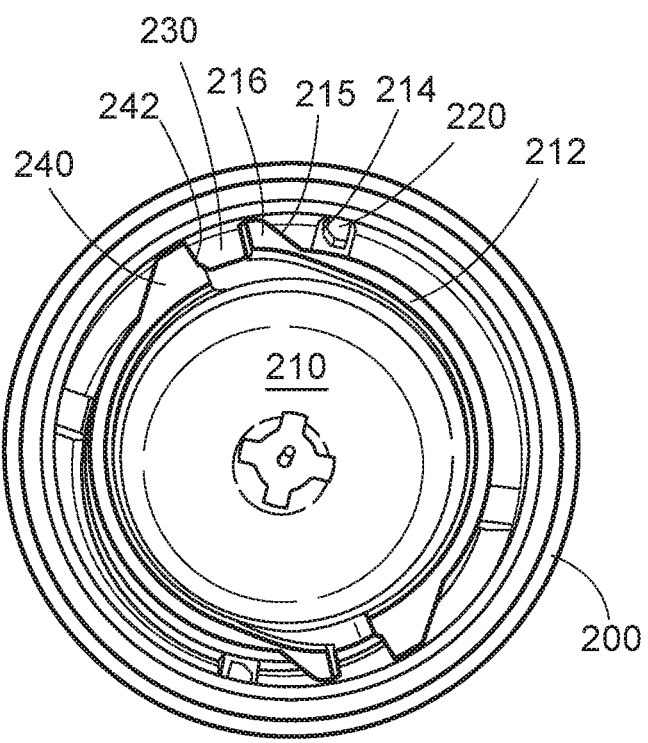
FIG. 22 and FIG. 23 depict interior views of a hub having a sensory feedback mechanism received in an outer cover according to embodiments of the invention.

Variation of the embodiments shown in FIG. 1 are depicted in FIG. 21A, FIG. 21B and FIG. 22, in which the engagement of hub 210 with shield 200 creates an initial audible and/or tactile sensation when hub 210 is fully seated on the injection pen, followed by a hard stop. For this purpose, at least one, and preferably a plurality of ribs 220 is provided on an inside surface of outer cover 200 engaging flexible tab 212 on hub 210. As shown in FIG. 21B, each of the plurality of ribs 220 includes an L-shaped surface 280. The L-shaped surface 280 is defined by a first face 211 that faces radially inward with respect to the hub 210. The L-shaped surface is further defined by a second face 213 that faces axially toward a proximal end of the outer cover 200. FIG. 22 shows hub 210 received in outer cover 200 according to an embodiment of the invention in which a beveled surface 214 on rib 220 and a second beveled surface 215 on projection 216 on flexible tab 212 permits rib(s) 220 to ride over projection 216, deflecting flexible tab 212. The recovery of flexible tab 212 after being deflected causes an audible and tactile sensation. Hard stop 240 has a height in the radial direction, and a surface 242 perpendicular to the circumferential direction, to prevent further rotation of outer cover 200 with respect to hub 210. A gap 230 between hard stop 240 and projection 216 on tab 212 accommodates a rib 220. As with the previous embodiment, one or more additional tab 212' may be utilized, in cooperation with one or more additional rib(s) 220. Unlike in the previous embodiment, clockwise rotation of shield 200 with respect to hub 210 is prevented after rib 220 abuts hard stop 240. There are slight differences in the construction of outer cover 200 and hub 210 in the embodiment of FIG. 21A and FIG. 21B compared to the assembly in FIG. 22. However, the overall concept is the same.

Figure 23:
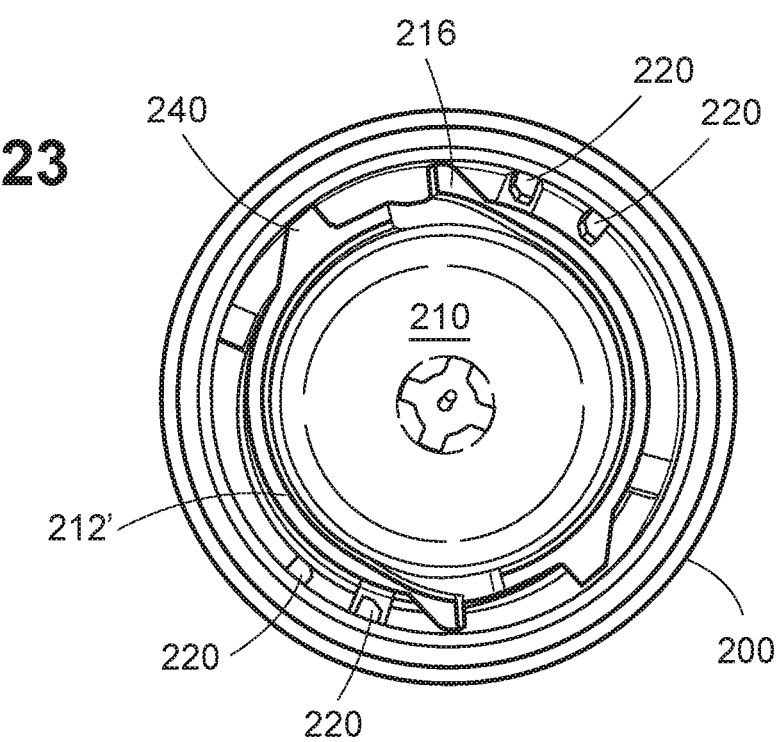
Figure 24:
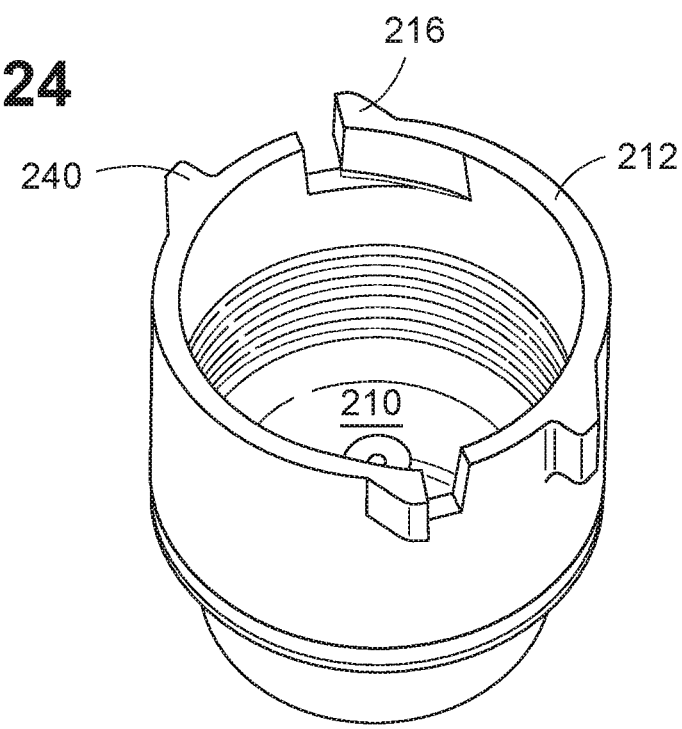
FIG. 24 shows an interior view of a hub.

In a variation shown in FIG. 23, two sets of two ribs 220 are provided on opposite sides of an inside surface of outer cover 200 having a first face 211 and a second face 213. The number, radial height and spacing of ribs 220, and stiffness of flexible tab 212 may be selected so that threading hub 210 onto a pen offers greater or lesser resistance and produces a louder or softer sound. The number and spacing of ribs 220 etc. also determines the quality of the ratchet like sound preceding the click that signals hub 210 is fully seated. Thus the embodiment of FIG. 22 will produce a click followed by a stop, the embodiment of FIG. 23 will produce two clicks followed by a stop. Providing sensory feedback in the form of three, four or more clicks followed by a stop is merely a matter of adding an additional rib 220 and selecting appropriate spacing between ribs 220.

Figure 25A:
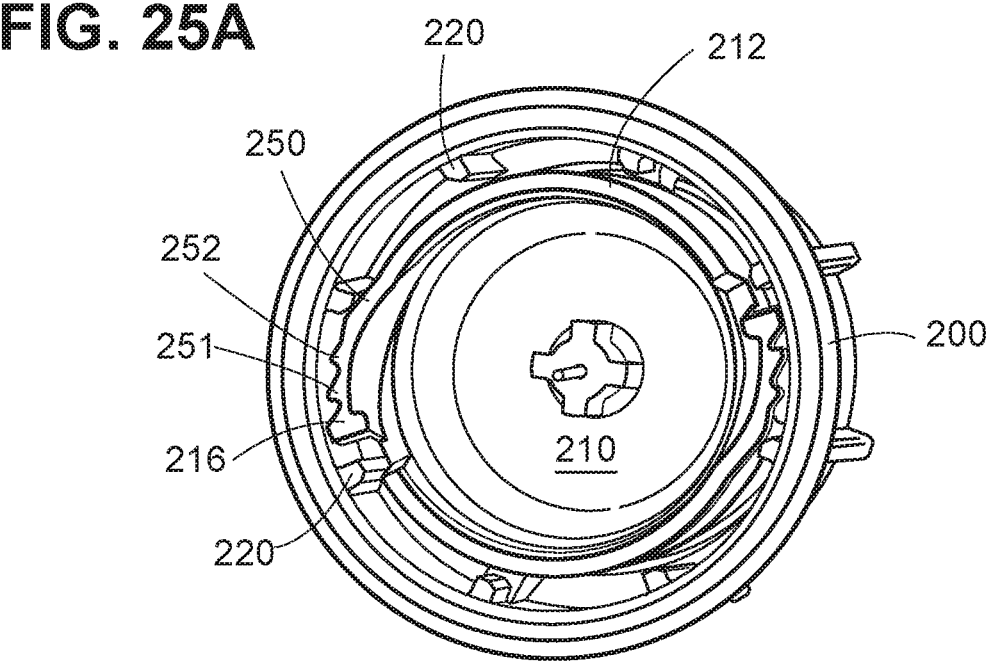
FIG. 25A shows an assembled hub and outer cover according to an embodiment of the invention.
Figure 25B:
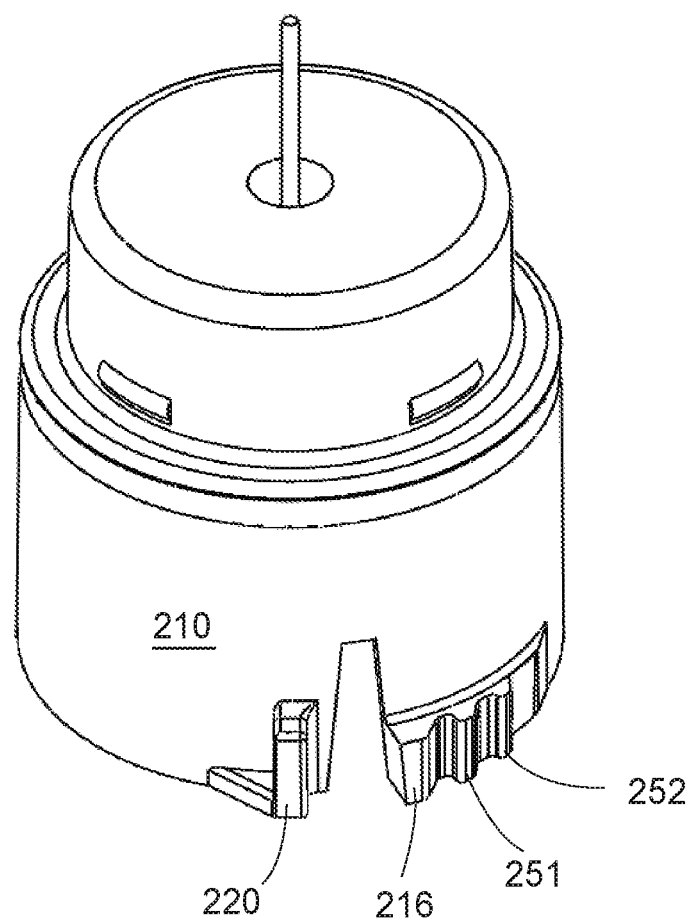
FIG. 25B is a hub adapted for the combination depicted in FIG. 25A.

In still another related embodiment, shown in FIG. 25A, and FIG. 25B flexible tab 212 has a ramped portion 250 sloping in the radially outward direction. As outer cover 200 rotates with respect to hub 210, rib(s) 220 ride along ramp 250. Depending on the degree of slope of ramp 250 and stiffness of tab 212, greater or lesser resistance is offered to threading hub 210 onto a medication pen as rotation progresses. In addition, or alternatively, a series of "washboard" projections 251, 252 may be provided at the end of flexible tab 250 so that a series of clicks are generated as rib(s) 220 ride over projection 220 before meeting hard stop 240.

In another embodiment, the invention comprises a pen needle comprising a needle bearing hub having a proximal end portion having an interior surface with threads for attachment to a medication delivery device; and a distal end portion, narrower than the proximal end portion, meeting the proximal end at a step portion, wherein the distal end comprises a flat distal end face, a side wall, and flexible radial projections extending from the side wall in a radially outward direction, adapted to be displaced by contact with an outer cover, and adapted to provide sensory feedback from engagement of the flexible radial projections on the hub with inwardly projecting ribs on the outer cover when the hub is installed on the medication delivery device.

Figure 19A:
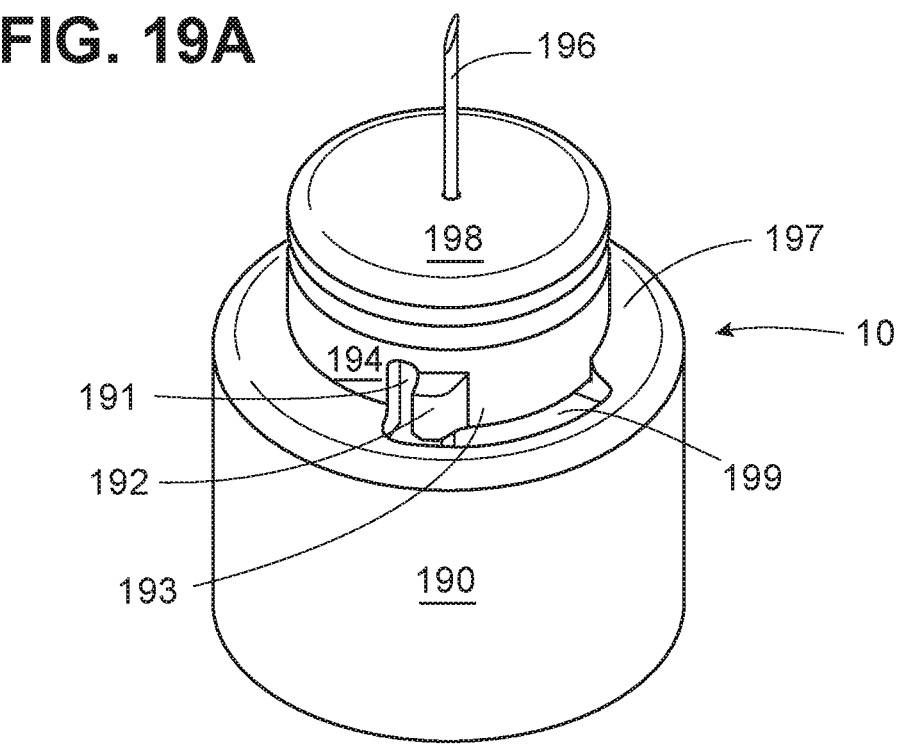
FIG. 19A is a view of a hub according to an embodiment of the invention and FIG. 19B depicts the top view of the hub of FIG. 19A.
Figure 19B:
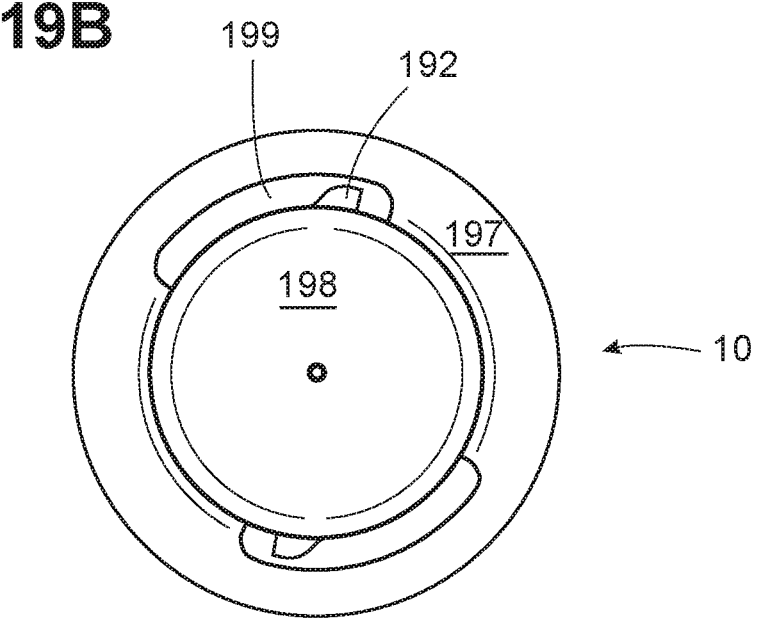

A variation of this stepped hub embodiment is shown in FIG. 19A and FIG. 19B. In this embodiment, hub 10 has a proximal end portion 190 for receiving a medication pen and a distal end portion 194 supporting needle 196. Distal end portion 194 has a distal end face 198, and proximal end portion 190 also has a distal end face 197 forming a step where distal end portion 194 meets proximal end portion 190. Opening 199 is formed in distal end face 197 of proximal end portion defining the proximal side of a strip 193 which flexes to allow flexible radial projections 192 to engage inwardly projecting rib(s) on the outer cover and also to simplify fabrication by conventional plastic draw molding techniques. A slit 191 extending axially from one end of opening 199 defines the end of strip 193. In embodiments, strip 193 is formed without a slit on its distal side to facilitate molding. Providing radially outward projection 12 at a step portion on hub 10 causes the sensory feedback mechanism to take up less space radially so that a slimmer profile outer cover may be used and the entire assembly may fit under the outer cap of a conventional medication pen.

Figure 20:
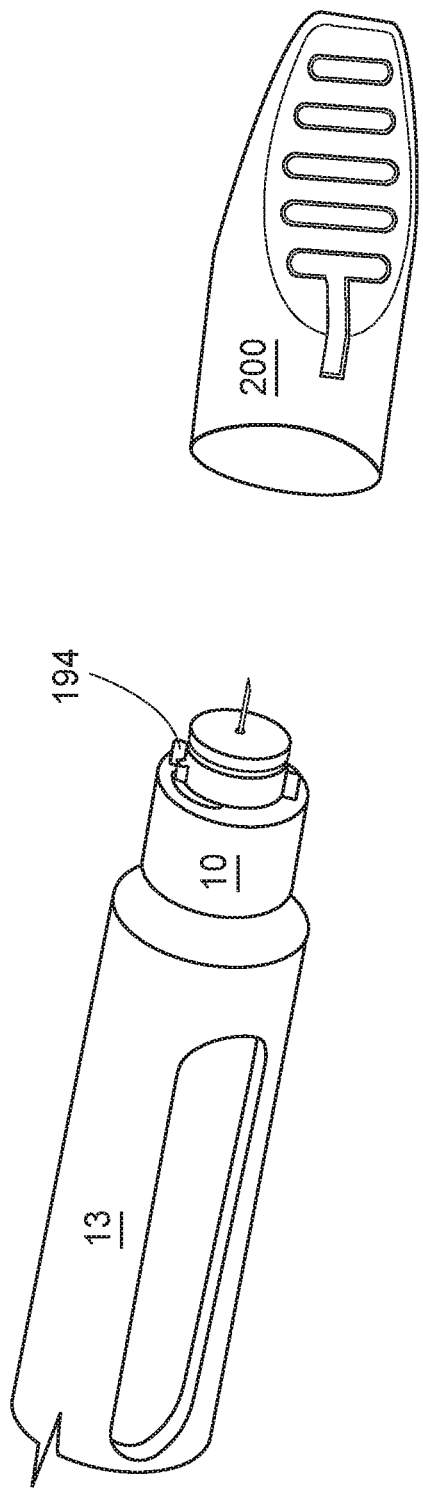
FIG. 20 depicts the hub of FIG. 19A attached to a medication pen, and an associated outer cover.

In the example of FIG. 20, hub 10 comprises a distal end portion 194 which is narrower than a proximal end portion attached to pen 13. Therefore, sensory feedback features are provided radially inwardly closer to the needle, and a pen cap 200 fits over hub 10 installed on a medication pen, without interfering projections on the base of hub 10.

Figure 4:
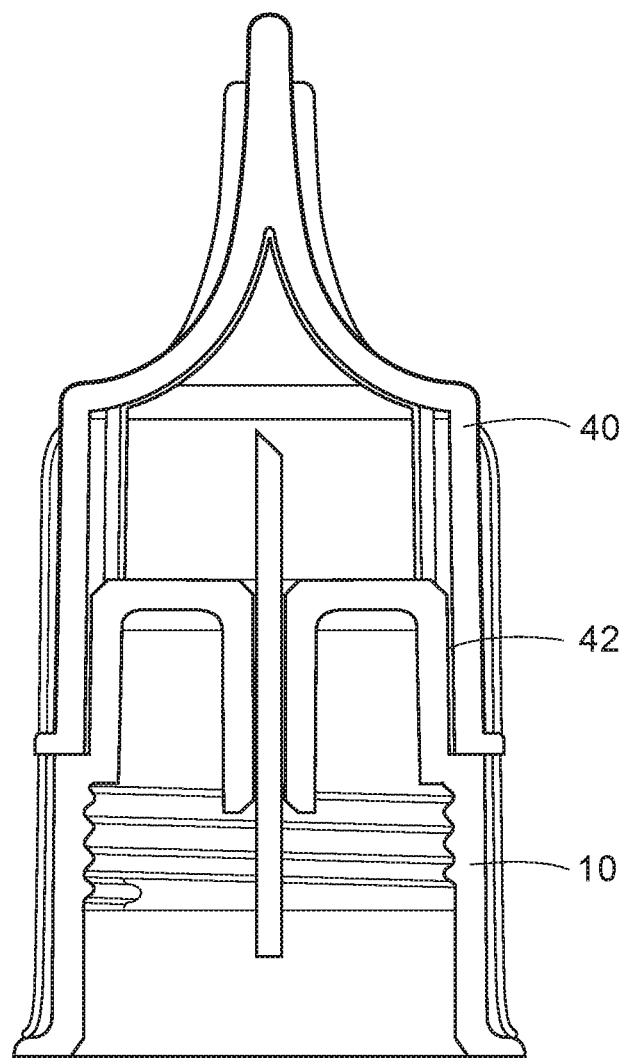
FIG. 4 depicts an outer cover assembled with a hub providing a sterile enclosure around the patient end needle using a tortuous path barrier and without using an inner needle cover, according to another embodiment of the invention.

FIG. 6 provides a view of hub 10 installed on medication pen 13, together with outer cover 20 and an inner shield 61, in an exploded view. This embodiment may include a stepped hub 10 attached to a medication pen 13. The hub 10 may have a wider proximal first portion 41 and a narrower distal second portion 11 meeting at a step 17 and having an outer edge 43. The proximal end of optional inner shield 61 is received over the narrower portion 11 of the hub. In the embodiment shown, the inner shield 61 is wider than a conventional inner needle shield, which makes gripping the piece easier for the user when removing the inner shield. Optionally, ribs 63 may be provided on the outer surface of inner shield 61 to facilitate gripping. Outer cover 20 is adapted to align its open end with the proximal non-patient end of the hub 10 which is attached to a medication pen 13. Ribs 22 engage flexible tab 12. As shown in FIG. 7, hub 10 and inner shield 61 are received inside outer cover 20 which may be closed off with foil tab 72 to form a sterile enclosure as a packaged unit 70. Outer cover 20 may be transparent to afford a view of the inner shield, although this is primarily an aesthetic choice. Flat patient-facing contact surface 69 on hub 10 may be obtained by recessing the needle support below the distal surface. This configuration is shown in the cross sectional view of FIG. 4. A hub with a flat pressure pad area is disclosed in U.S. Patent Application Publication No. 2009/0069755, incorporated by reference.

Figure 2A:
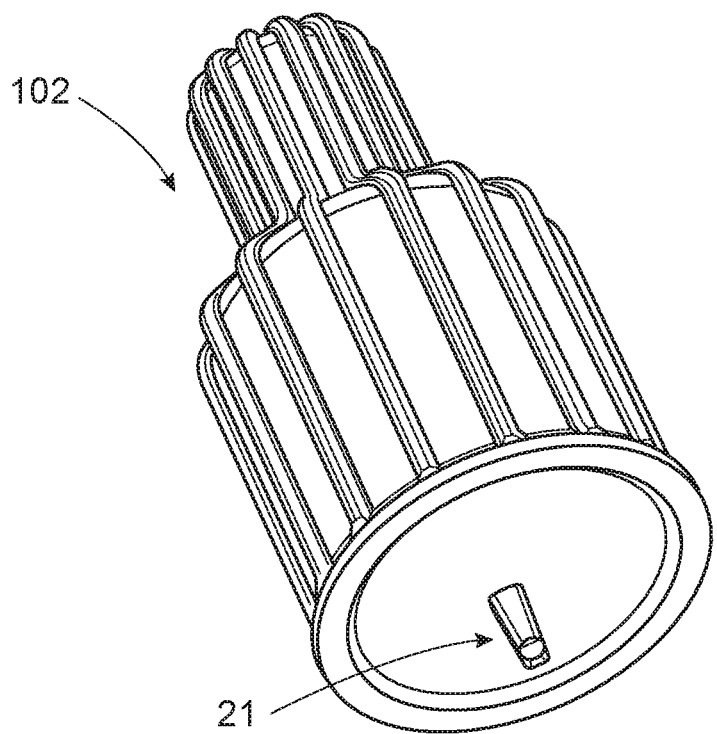
FIG. 2A depicts an outer cover according to another embodiment of the invention.
Figure 2B:
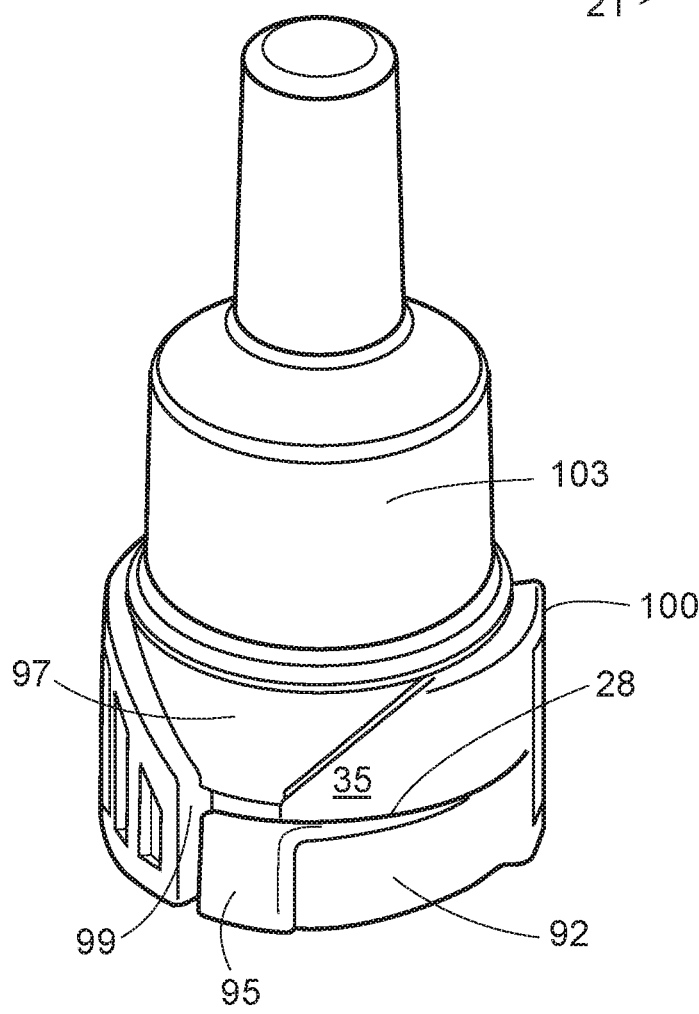
FIG. 2B depicts the hub adapted to be retained in the outer cover shown in FIG. 2A.
Figure 3:
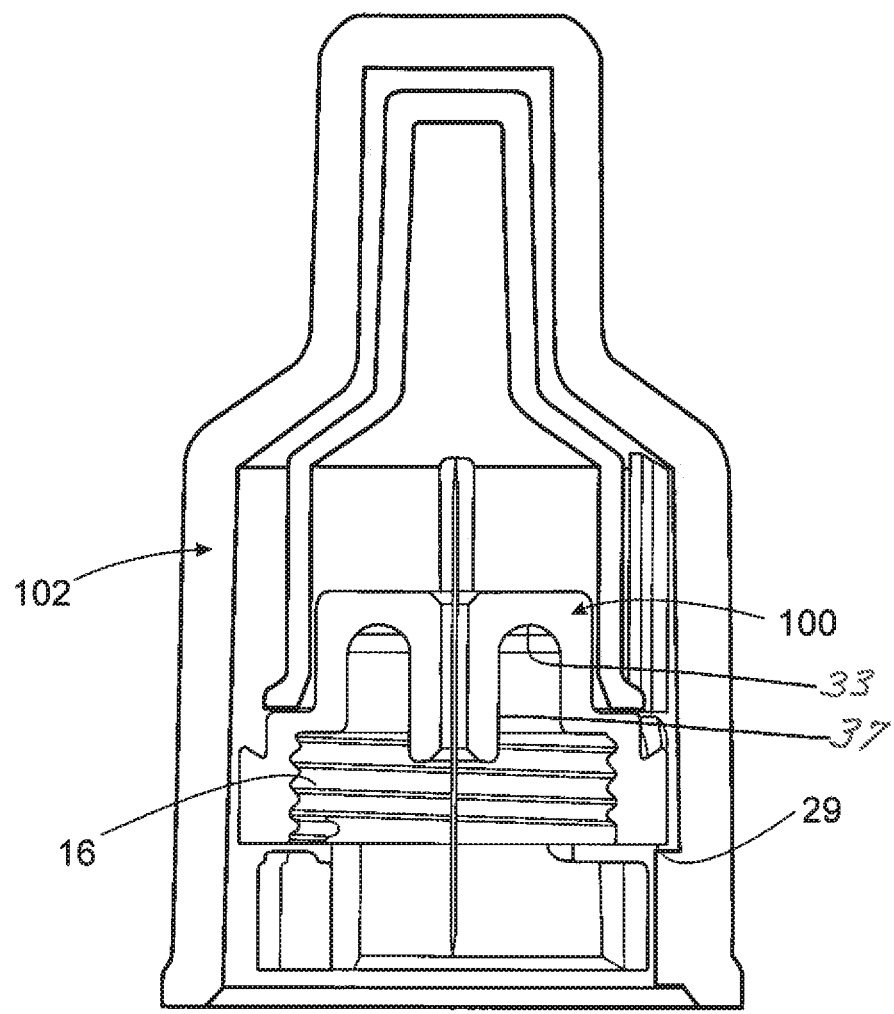
FIG. 3 depicts a cross sectional view of the assembly of FIG. 2A and FIG. 2B.

Another embodiment according to the invention also incorporates a flexible tab located proximally of the threads on the hub, and having an outward projection as depicted in FIGS. 2A, 2B, and 3. As in the preceding embodiment, a hub is provided having a cavity on a proximal end thereof with threads for rotating the hub securely onto a medication pen. In this embodiment, outer cover 102 is initially prevented from moving in a distal direction, and snaps into a position from which it can be removed from the hub after the hub has been fully seated on the medication pen.

To achieve engagement between outer cover 102 and hub 100, hub 100 is provided with a circumferentially oriented flexible tab 92 located near threads 16 (shown in FIG. 3). Hub 100 has an inner face 33, and needle-bearing post 37, a radially outward surface including an increased diameter step portion 35. The step portion 35 forms a locking surface 29 on the hub, perpendicular to the axis of the needle, which engages an inwardly projecting locking rib 21 on outer cover 102 to prevent outer cover 102 from moving distally so long as the locking surface 29 engages the locking rib 21. Outer cover 102 received on hub 100 has a closed distal end, an open proximal end, and a locking rib 21 at the open proximal end projecting radially inwardly. Locking rib 21 engages locking surface 29, so that the outer cover may rotate, but is prevented from moving distally. Flexible tab 92 has a radially outward surface with a projection 95 projecting from an end of the flexible tab and positioned at one end of the locking surface 29. Locking rib 21 engages the projection 95 on the flexible tab on the hub and causes the outer cover to rotate together with the hub while the hub is threaded onto the medication pen. However, when the hub is fully seated on the medication pen, and enough force is applied against the projection 95 by the locking rib 21, the locking rib rides over the projection on the flexible tab and the tab is deflected radially inwardly.

With the tab deflected inwardly, locking rib 29 is positioned at the bottom of a funnel shape 97 formed by two opposed sloping surfaces having increased diameter (a raised height in a radial direction compared to the area of funnel shape 97) converging toward a release channel 99. In this position, locking surface 29 no longer interferes with rib 21 and outer cover 102 can be removed by pulling distally. Flexible tab 92 snaps back behind locking rib 21 when locking rib 21 reaches this position, providing the user with an audible and/or tactile indication that the hub 100 is installed and fully seated on the medication pen. Replacing the outer cover over the patient-end needle of hub 100 is facilitated by the opposed sloping surfaces forming the funnel shaped area 97. Locking rib 21 is guided to the release channel 99, where it can then be rotated back into abutting engagement with locking surface 29 for removal of the hub from the medication pen by rotating in a counter-clockwise direction. As shown in FIG. 2B, inner cover 103 is provided over the needle in an initial state, removed prior to performing an injection.

In another aspect of the invention, a tortuous path sterile barrier is provided between an inner shield and a hub, or between an outer cover and a hub (eliminating an inner shield altogether). In the embodiment shown in the cross-sectional view of FIG. 4, outer cover 40 abuts a step portion on hub 10. Outer cover 40 is sealed to hub 10 with a tortuous path barrier 42, ensuring sterility of the needle and eliminating a conventional inner shield. A foil or paper-foil flexible cover in this embodiment is heat sealed directly to the open proximal edge of hub 10, instead of to the outer cover. The complete assembly 130 is shown in FIG. 14, and the installation of this embodiment on a medication pen is shown in FIG. 13. Using a hub having a wider proximal portion and a narrower distal portion permits the outer cover to abut the hub securely and forms a sterile barrier with the hub by means of a labyrinth seal. The concept of a labyrinth seal is well known in the biomedical devices art, and simply means that airborne organisms are presented with a tortuous path which prevents the organisms from contaminating the enclosed space around the cannula, thereby ensuring sterility. The barrier forms a type of seal which must be broken by the user before use but the force required is not so great as to cause inconvenience. This concept is elaborated upon in U.S. Patent Application Publication No. 2012/0041381, incorporated by reference.

Figure 5:
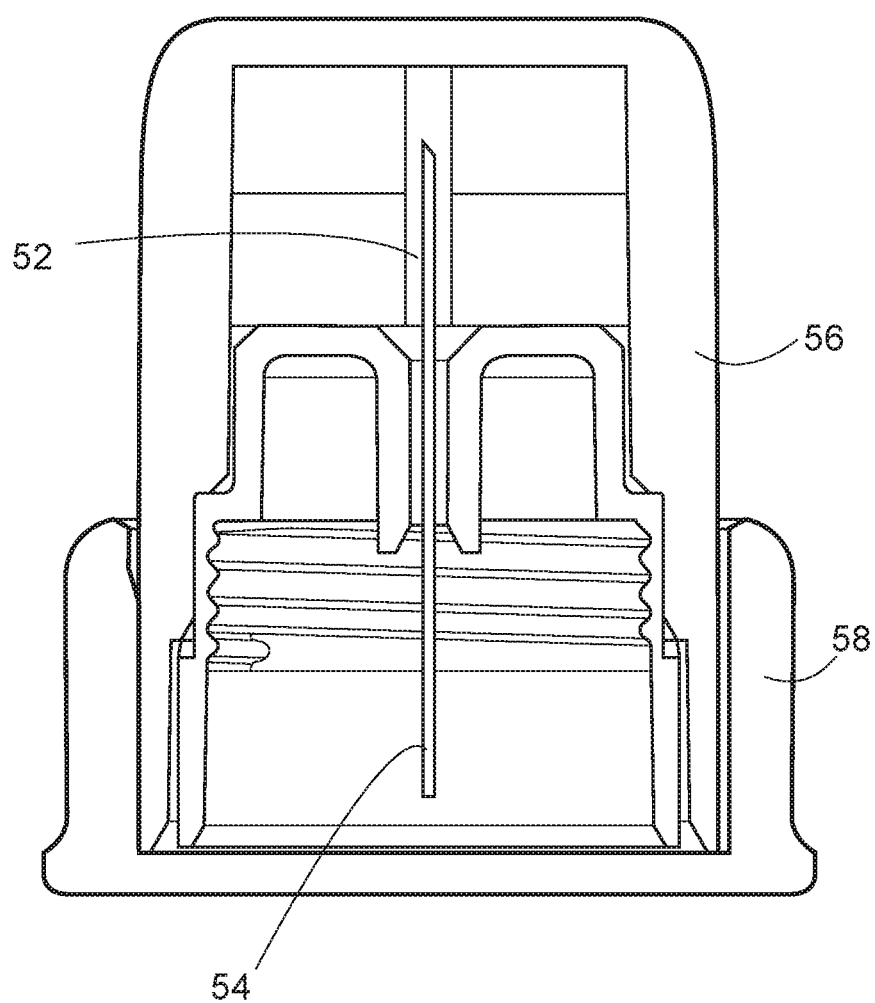
FIG. 5 depicts an outer cover assembled with an outer cap on the proximal end thereof according to another embodiment of the invention.
Figure 8:
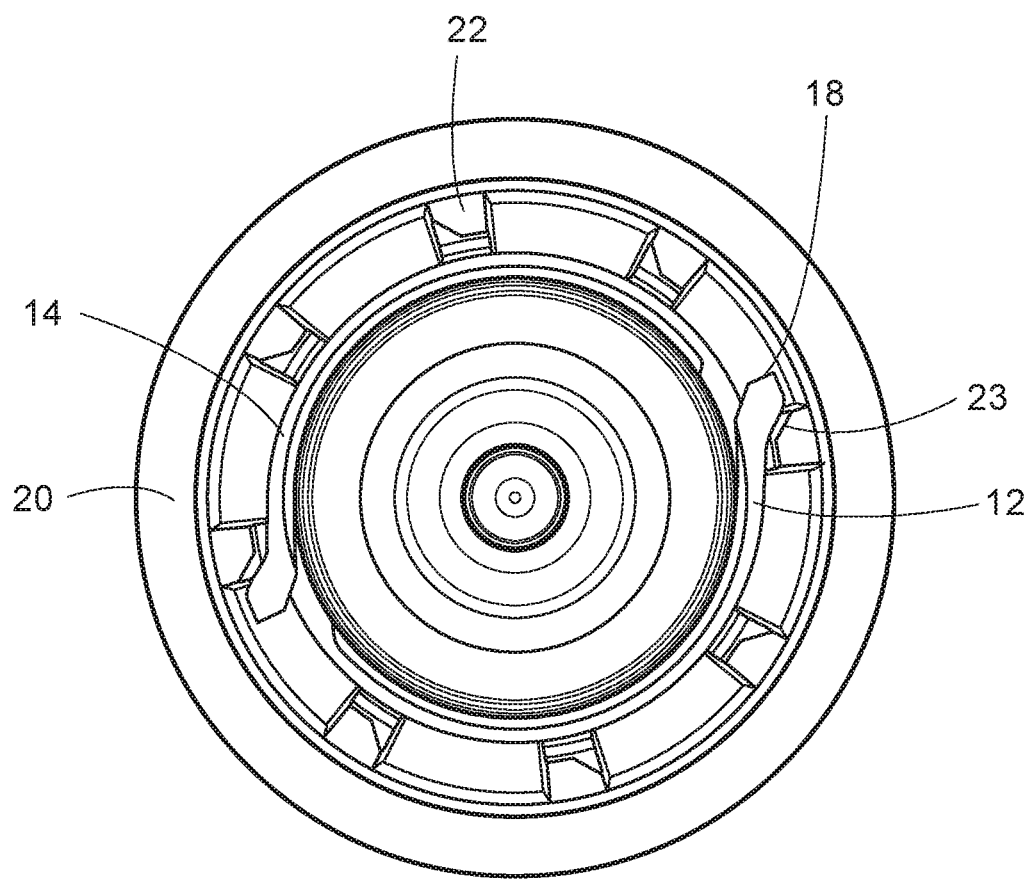
FIG. 8 is a cross sectional view of the assembly of FIG. 1 from an axial perspective.
Figure 11:
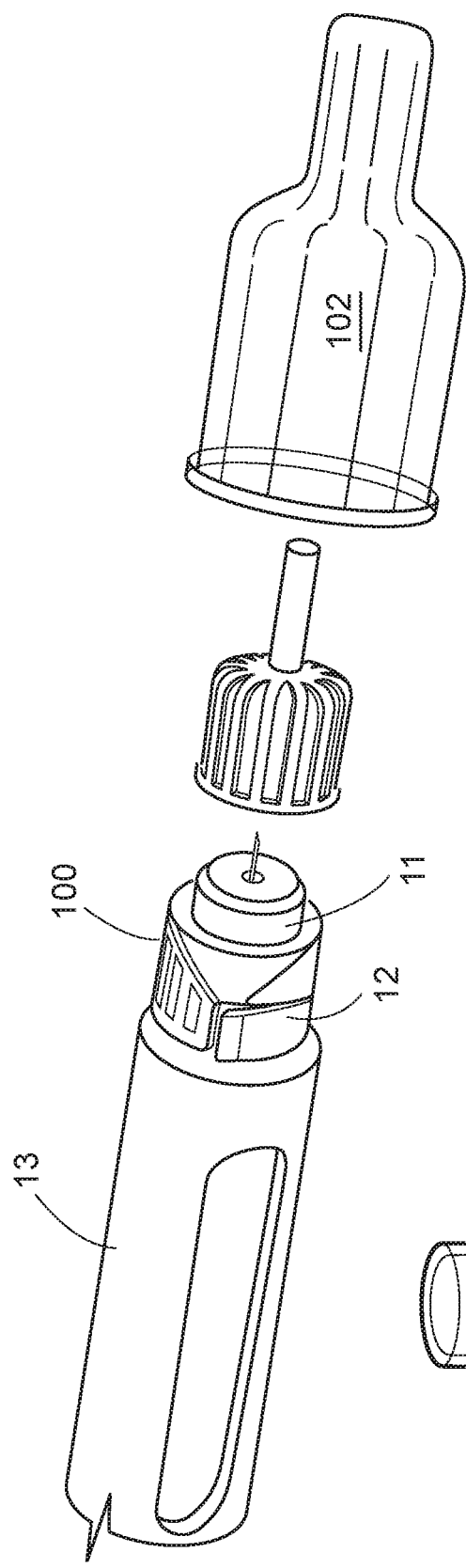
FIG. 11 is an exploded view of medication pen and pen needle assembly incorporating the outer cover and hub assembly of FIGS. 2A and 2B.
Figure 12:
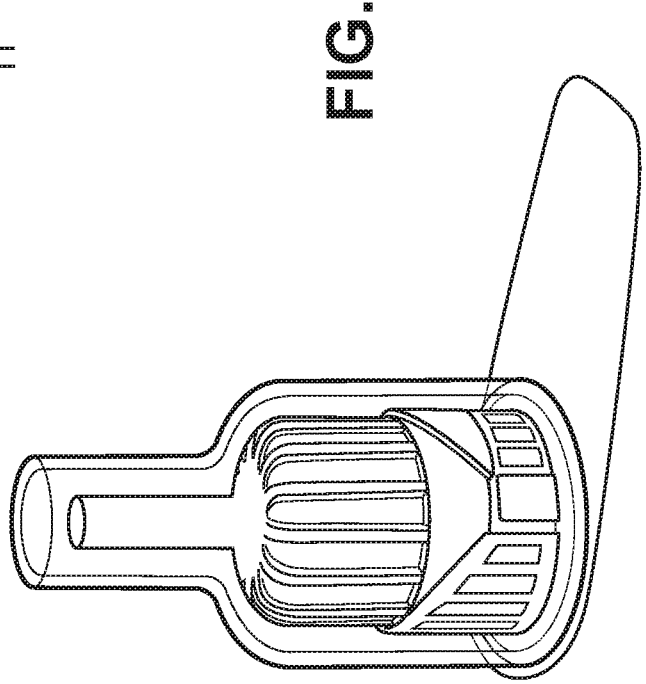
FIG. 12 is a perspective view of the pen needle and outer cover assembly of FIG. 2A and FIG. 2B in sterile packaging.

Yet another embodiment incorporating a tortuous path barrier is depicted in FIGS. 5, 9, and 10, wherein a needle bearing hub having a patient end needle 52 and non-patient end needle 54 is enclosed in a distal outer cover 56 and a proximal outer cap 58. Distal outer cover 56 and proximal outer cap 58 are sealed with a labyrinth seal to form a sterile enclosure around the non-patient end needle and the patient end needle prior to use. This configuration obviates the need for the paper-foil tear drop label and may be preferable for patients who cannot easily manipulate small objects. Grips 92, 94 on distal outer cover 56 and proximal cap 58, and a shaped surface on the distal outer cover may be provided to improve the user's grip on the pen needle to facilitate breaking the tortuous path barrier.

Figure 15:
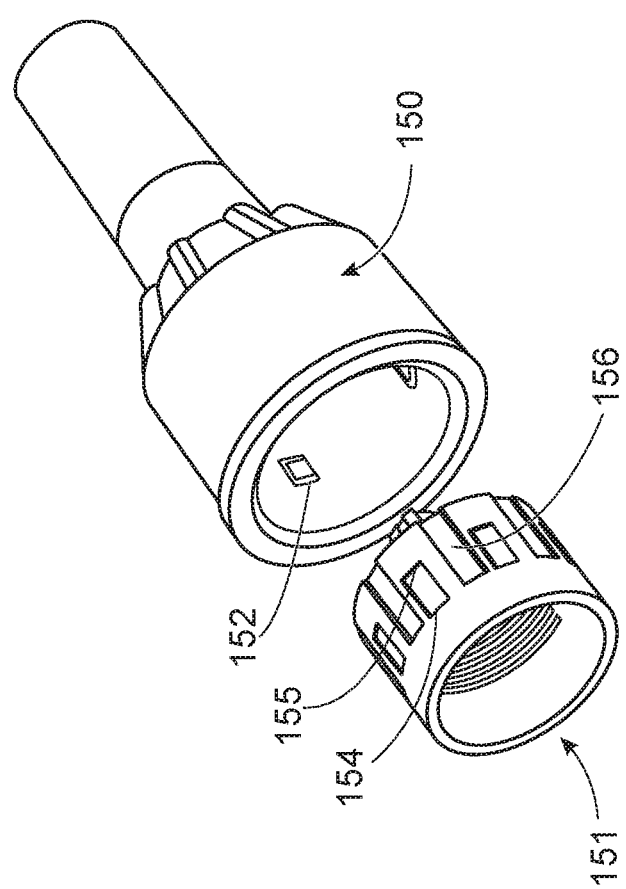
FIG. 15 depicts a pen needle outer cover assembly according to another embodiment of the invention.
Figure 16:
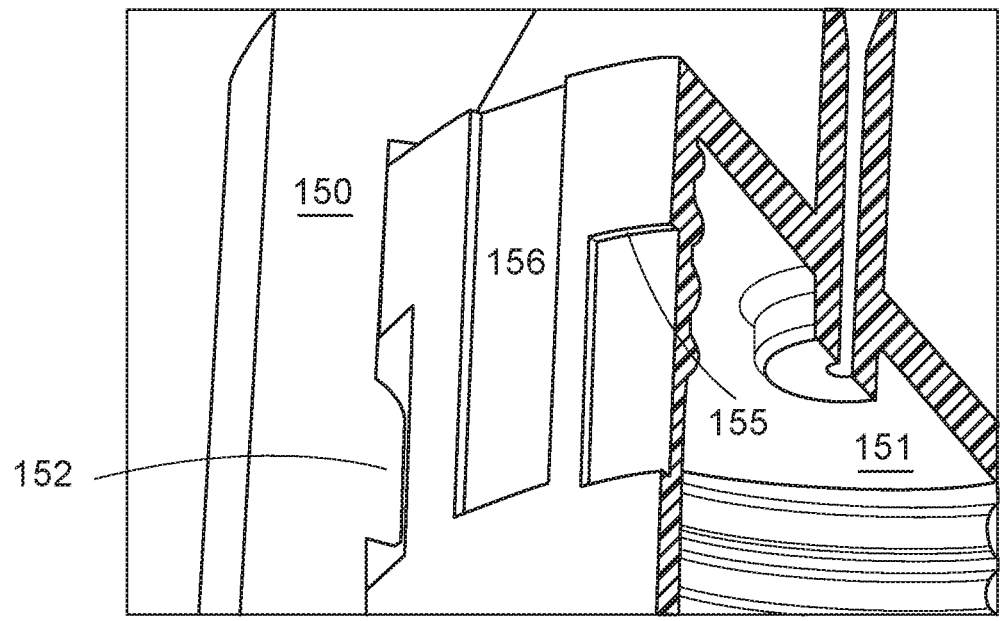
FIG. 16 depicts a detail of the embodiment of FIG. 15 with the outer cover engaged to the hub in a locked position.
Figure 17:
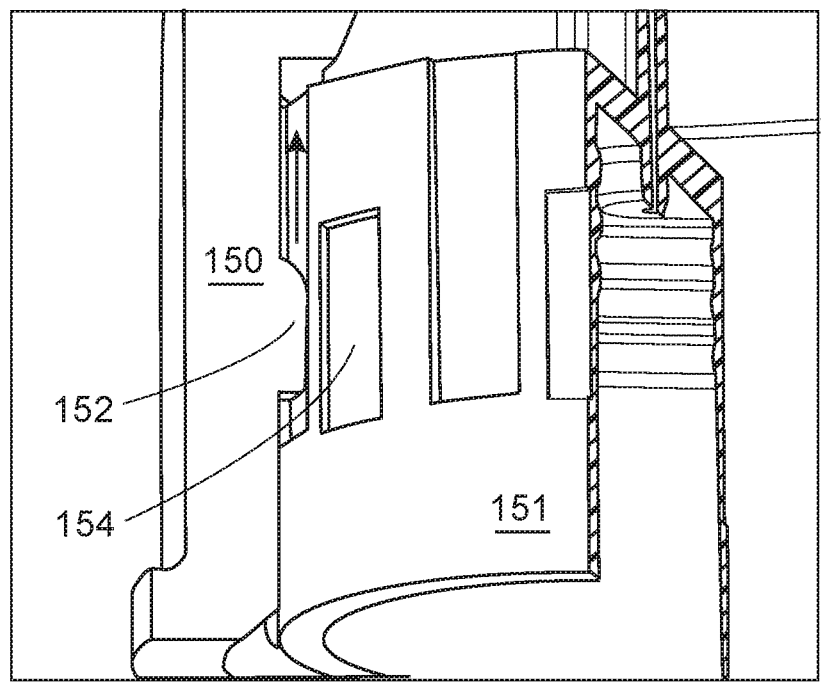
FIG. 17 depicts a detail of the embodiment of FIG. 15 with the outer cover engaged to the hub in a released position, capable of distal movement with respect to the hub.

According to an embodiment of the invention depicted in FIGS. 15, 16, and 17, outer cover 150 is provided with at least one projection 152 on a radially inward surface. Hub 151 (shown here without the cannula) has a cavity on a proximal side thereof with threads for receiving a medication pen. An outer surface of hub 151 has at least one inboard slot 154 having a distal edge 155. As shown in FIG. 16, distal edge 155 of inboard slot 154 prevents projection 152 from moving distally in a first locked position when projection 152 is engaged in inboard slot 154. When the outer cover and hub are rotated clockwise, the hub and outer cover rotate together until the hub is seated on the medication pen. After the hub is seated, sufficient force develops between the outer cover and the hub so that the outer cover rotates with respect to the hub, and projection 152 engages open ended slot 156 as shown in FIG. 17. In this position the outer cover is free to move distally. Preferably, a plurality of inboard slots 154 and a plurality of open ended slots 156 are interspersed on the radially outward surface of the hub for engagement with the outer cover. Preferably, the outer cover is provided with a plurality of symmetrically arranged protrusions, guiding smooth distal movement of the outer cover in a plurality of respective slots. Two, and preferably three, four or more protrusions 152 may be provided for this purpose.

Figure 18A:
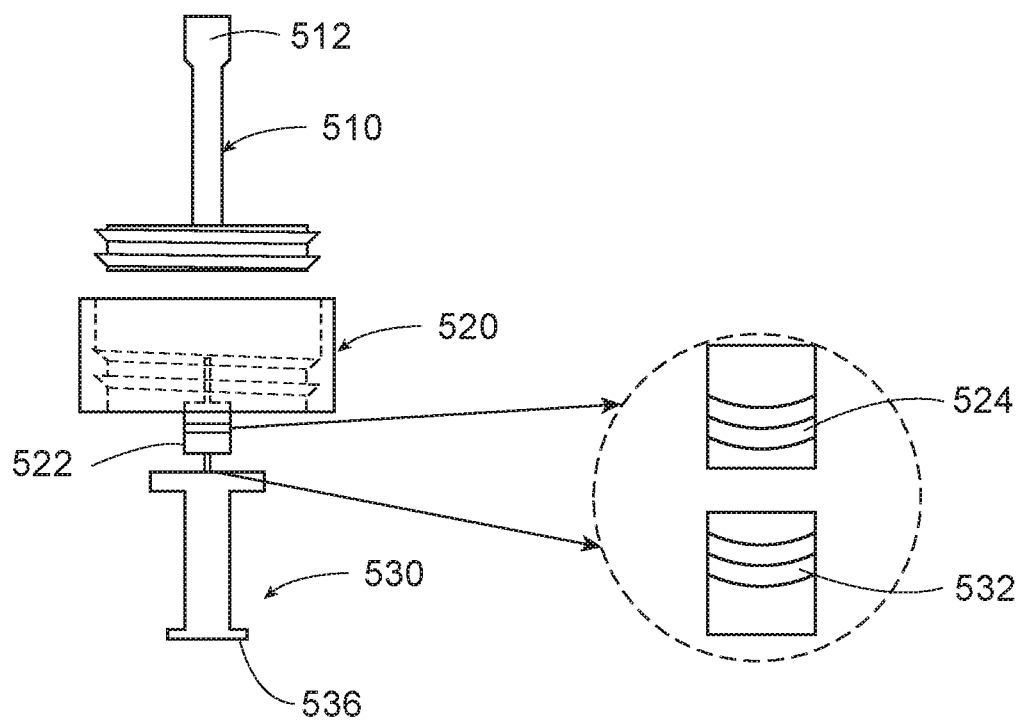
FIG. 18A is an exploded view according to another embodiment of the invention, wherein the patient end shield and the non-patient end shield extend from the hub in a spindle configuration.
Figure 18B:
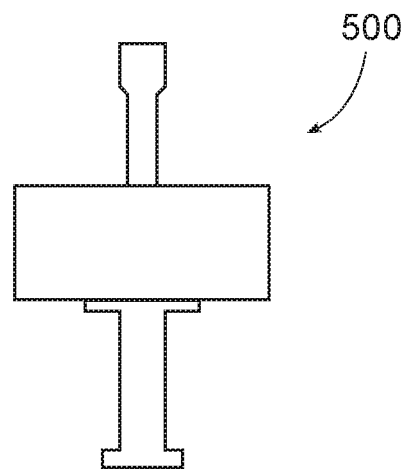
FIG. 18B depicts an assembled version of the embodiment of FIG. 18A.

In the embodiments depicted in FIG. 18A and FIG. 18B, a pen needle according to the invention takes the appearance of a spindle, with two relatively narrow cylindrical needle shields 510, 530 received over the non-patient end cannula and the patient end cannula respectively. The shields may be on the order of one-third to one-tenth the diameter of the hub, such that the functionality of the shields as needle covers is immediately apparent to the user. Threads on an interior surface of the non-patient end of the hub 520 mate with threads on a laterally extending disk-shaped member on the non-patient end shield 510 to provide a sterility barrier around the area of the non-patient end cannula. Label information may be provided on the narrow cylindrical portion of the non-patient end shield using laser marking. A laser marking additive may be added to the polymer molded to make the part, as known in the art.

Sterility around the patient end needle may be provided by a tortuous path barrier, which prevents airborne microorganisms from contaminating the area, but which can be pulled off. As depicted in FIG. 18A, the hub 520 is provided with an axially located hub post 522 on which the cannula is secured. As shown in the inset diagram, the patient side shield 530 is provided with a first contour 532 on an interior surface that mates with a contour 524 on the outward surface of hub post 522 to provide a sterile seal which, unlike the threaded connection on the non-patient side, can be broken when sufficient force is applied to detach the shield from the hub. As shown in the inset of FIG. 18A, the tortuous path forming surface on the hub may be formed on a hub post, which is a conventional needle bearing member on the hub. The patient-side shield may have a shape similar to the conventional patient side shield, which is cylindrical and relatively thin, so that the function of the element as a needle shield is intuitively clear to the user. An assembled view of the pen needle 500 is provided in FIG. 18B, wherein, both the patient side shield and the non-patient side shield are narrow cylinders relative to the cylindrical outer periphery of the hub, so that the shields and hub together resemble a spindle when the device is assembled. The use of smaller shield elements is expected to reduce materials costs. The proximal end of the non-patient side shield in turn may be provided with small extensions 512 which provide a grip to provide for unscrewing the member from the hub.

The order of removing the shields around the cannula is effectively predetermined, because the shield on the patient side is only readily pulled off after the hub 520 is installed on the medication pen. In the embodiment shown in FIG. 18A, non-patient side shield 510 has a flat portion formed by extension 512 to allow for disengaging the threads at the interface of the shield and hub. The user is expected to unthread the non-patient end shield 510 first. The user can pull off the patient end shield by grasping the medication pen with the pen needle installed and using the leverage created by the attachment of the medication pen to the hub to break the sterility barrier and remove the patient end shield. The distal end of the patient-side shield may likewise be provided with a lateral extension 536 to facilitate pulling the shield off the hub post.

In each of the foregoing embodiments, the components of the hub and outer cover are typically injection molded plastic, such as acrylonitrile butadiene styrene (ABS), polypropylene, or the like while the cannula is surgical grade stainless steel. Other materials and methods of manufacture known to those of ordinary skill in the art of medication pen technology may be adapted for use herein without departing from the scope of the invention. To assemble the parts, the hub assembly may be constructed with the needle separately, with adhesive applied in the interface area to secure the cannula to the hub, and this sub-assembly may then be assembled with an inner shield (optionally, depending on the embodiment), and fit by interference into an outer cover.

The foregoing description of the preferred embodiments is not to be deemed limiting of the invention, which is defined by the following claims. The foregoing description should provide the artisan of ordinary skill with sufficient information to practice variants of the embodiments described. Features and improvements described in dependent claims or in connection with one embodiment may be combined with another independent claim or another embodiment without departing from the scope of the invention.

The invention claimed is:

1. A pen needle, comprising:
   a hub having a first portion with a substantially cylindrical shape and threads for attachment to a medication delivery device, a second portion having a diameter less than a diameter of said first portion, a step between said first portion and said second portion, a needle extending from said second portion, a patient-facing surface at a distal end of said second portion of said hub, an inner face opposite said patient-facing surface, and an elongated post extending from said inner face into said hub and supporting said needle in said hub, and where said patient-facing surface has a flat surface where said patient-facing surface extends between said needle and an outer edge of said second portion; and
   an inner shield received on said second portion, and an outer cover received over said first portion of said hub, said outer cover having a side wall with an inner surface and a plurality of ribs projecting radially inward from said inner surface, wherein said plurality of ribs have L-shaped surfaces, the L-shaped surfaces comprising first faces facing radially inward with respect to said hub and second faces facing axially toward a proximal end of said outer cover.

2. The pen needle according to claim 1, wherein said distal end is defined by said patient-facing surface and said hub has a proximal end, wherein said threads are spaced axially from said inner face.

3. The pen needle according to claim 2, wherein said elongated post extends from said inner face by a distance greater than a distance between said inner face and said threads.

4. The pen needle according to claim 1, wherein said patient-facing surface has a width corresponding substantially to a width of said flat surface of said distal end of said second portion of said hub, and wherein said needle extends from said patient-facing surface and said elongated post extends in a direction opposite said patient-facing surface.

5. The pen needle according to claim 1, wherein said threads are positioned at a distal end of said first portion.

6. The pen needle according to claim 1, wherein said first portion of said hub has an outer surface with a plurality of open slots facing radially outward, and wherein said plurality of ribs are configured to engage said plurality of open slots.

7. The pen needle according to claim 6, wherein said plurality of ribs deflect and slide over said plurality of open slots by rotation of said outer cover with respect to said hub to produce a sensory feedback.

8. The pen needle according to claim 1, wherein said first portion of said hub has a flexible tab located proximally of said threads and extends circumferentially with respect to said hub, and where said plurality of ribs deflect said flexible tab when said outer cover rotates with respect to said hub to produce an audible feedback.

9. A pen needle comprising:
   a hub having a side wall having a first portion with an inner surface having threads for attachment to a medication delivery device, a second portion with a diameter less than a diameter of said first portion, a step between said first portion and said second portion, and a needle extending from said second portion, said first portion of said hub has an outer surface with a plurality of open gaps facing radially outward;
   an inner shield received on said second portion and covering said needle, and
   an outer cover received over said first portion of said hub covering the inner shield and having a plurality of ribs, said ribs axially extending and having L-shaped surfaces, the L-shaped surfaces comprising first faces facing radially inward toward said first portion of said hub, and second faces facing axially toward a proximal end of said outer cover, and wherein said plurality of ribs deflect and slide over said plurality of open gaps by rotation of said outer cover with respect to said hub to produce a sensory feedback.

10. The pen needle according to claim 9, wherein said second portion of said hub has a distal end defined by a patient-facing surface and a proximal end, said hub further comprising an elongated post extending from an inner axial surface at said distal end toward said proximal end, said elongated post supporting said needle in said hub.

11. The pen needle according to claim 9, wherein a distal end of said hub has an outer axial surface forming a patient-facing surface and an inner axial surface, and where an elongated post extends from said inner axial surface and said needle extends from said patient-facing surface.

12. The pen needle according to claim 11, wherein said threads are spaced axially from said inner axial surface of said hub.

13. The pen needle according to claim 12, wherein said elongated post extends from said inner axial surface a distance greater than a distance between said inner axial surface and said threads.

14. The pen needle according to claim 13, wherein said patient-facing surface has a flat surface extending from said needle toward an outer edge of said second portion, where said needle extends from said flat surface, and said elongated post extends in a direction opposite said patient-facing surface.

15. The pen needle according to claim 14, wherein said elongated post has a length greater than a length of said second portion.

16. The pen needle according to claim 15, wherein said threads are positioned at a distal end of said first portion.

* * * * *